United States Patent [19]
van den Akker et al.

[11] Patent Number: 6,069,274
[45] Date of Patent: May 30, 2000

[54] PROCESS FOR THE PREPARATION OF CHLORO-BENZOYLCHLORIDES

[75] Inventors: Laurens Wilhelm van den Akker, Karel Doormanlaan, Netherlands; Monika Brink, Albert-Schweitzer Strasse, Germany

[73] Assignee: American Cyanamid Company, Madison, N.J.

[21] Appl. No.: 09/005,871

[22] Filed: Jan. 12, 1998

Related U.S. Application Data

[60] Provisional application No. 60/044,813, Apr. 25, 1997.

[51] Int. Cl.$^7$ .................................................. C07C 51/58
[52] U.S. Cl. ............................................................. 562/859
[58] Field of Search .............................................. 562/859

[56] References Cited

U.S. PATENT DOCUMENTS 1,557,154  10/1925  George .
1,870,601  8/1932  Brtton et al. .

*Primary Examiner*—Paul J. Killos
*Attorney, Agent, or Firm*—Timothy J. Babcock

[57] ABSTRACT

An effective and efficient process for the preparation of chloro-benzoylchlorides of formula I,

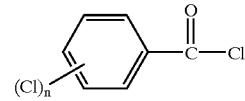

(n is defined in the specification).

In this process a a chloro-trichloromethylbenzene of formula II

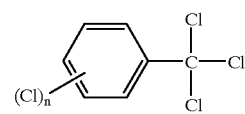

is treated with water acid in the presence of a Lewis at temperatures below 80° C. The compounds obtained according to this process can be used to prepare certain chloro-substituted benzophenones.

5 Claims, No Drawings

PROCESS FOR THE PREPARATION OF CHLORO-BENZOYLCHLORIDES

Priority is claimed by provisional application No. 60/044,813 filed Apr. 25, 1997.

BACKGROUND OF THE INVENTION

The present invention relates to a process for the preparation of chloro-benzoylchlorides from a chloro-trichloromethylbenzene in which said chloro-trichloromethylbenzene is treated with water in the presence of a Lewis acid at temperatures below 80° C.

Chloro-trichloromethylbenzene compounds are suitable intermediates for the preparation of a broad variety of compounds which are useful as agrochemicals, pharmaceuticals or liquid crystals. In particular, they are key intermediates in the preparation of fungicidal dimethomorph (e.g. EP 0 120 321) and fungicidal benzophenones which are described for example in EP 0 727 141 A.

The German patent no. 331696 (Jul. 17, 1914) discloses a process wherein trichloromethylbenzene is treated with equimolar amounts of water in the presence of $FeCl_3$ at elevated temperatures to form benzoylchloride.

However, this process is hardly applicable in technical scale since it causes problems with respect to the dosing rate and the exact equimolar dosing of water at elevated temperatures. Any excess of water will cause hydrolysis of the desired acid chloride compound and therefore reduce the yields.

SUMMARY OF THE INVENTION

The present invention provides an effective and efficient process for the preparation of chloro-benzoylchlorides of formula I,

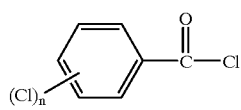

(I)

wherein
n represents an integer of 1, 2 or 3,
from a chloro-trichloromethylbenzene of formula II

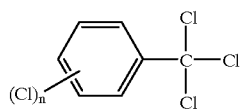

(II)

wherein n has the meaning given,
the improvement wherein is that the trichloromethylarene is treated with water acid in the presence of a Lewis acid at temperatures below 80° C.

It is, therefore, an object of the present invention to provide an efficient new process for the preparation of chloro-benzoylchloride compounds.

Other objects and advantages of the present invention will be apparent to those skilled in the art from the following description and the appended claims.

DETAILED DESCRIPTION OF THE INVENTION

Further preferred embodiments of the process according to the present invention is a process wherein:

the reaction is carried out without organic solvent;
the Lewis is $FeCl_3$,
the reaction mixture essentially consisting of the chloro-trichloromethylbenzene of formula II and the Lewis acid is heated up to temperatures below 80° C. and water is slowly added into the stirred solution;
the chloro-trichloromethylbenzene is a mono- or dichloro-trichloromethylbenzene, in particular 4-chloro-trichloromethylbenzene or 2,6-dichloro-trichloromethylbenzene;
1 mole of trichloromethylarene of formula II is treated with 0.8 to 1.2, preferably 0.9 to 1.1, in particular about 1 moles of water;
1 mole of trichloromethylarene of formula II is treated with water in the presence of 0.05 to 5 mol-%, preferably 0.1 to 3 mol-% of the Lewis acid.

The reaction is carried out at a temperature between ambient temperature and 80° C., preferably between 40 and 80° C., in particular between 45 and 65° C.

As a rule the reaction can be carried out under reduced or elevated pressure, preferably it is carried out under atmospheric pressure.

In a particularly preferred embodiment of the process according to the invention 1 equivalent of 4-chloro-trichloromethylbenzene, is mixed with 0.1 to 3 mol-% of the Lewis acid, in particular $FeCl_3$ and heated to 45 to 65° C., in particular 50 to 60° C. Then about 1 equivalent of water is dosed into this reaction mixture, which is kept at this temperature. The hydrochloric acid formed during the reaction is evolved out until the reaction is completed.

Under this preferred reaction conditions the reaction is as a rule completed within 0.25 to 5, in particular 1 to 4 hours.

The remaining aroyl chloride can be used as intermediate for the preparation of the desired end-products without further purification. In a particularly preferred embodiment the reaction mixture obtained can be used for the preparation of certain chloro-substituted benzophenone derivatives under Friedel-Crafts acylation conditions, in particular of formula III,

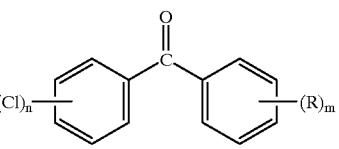

(III)

in which n has the meaning given, and
R each independently represents $C_{1-6}$ alkyl or $C_{1-6}$ alkoxy, and
m is an integer from 2 to 4,
under Friedel-Crafts acylation conditions by adding a Lewis acid and the corresponding substituted benzene derivative, preferably of formula IV,

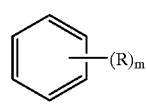

(IV)

in particular 1,2-dimethoxybenzene, 3,4,5-trimethoxytoluene or 3,4-dimethoxy-5-butoxytoluene, to said reaction mixture.

It is also possible to purify the obtained chlorobenzoylchlorides using standard procedures, as for example crystallization or distillation, in particular by distillation under reduced pressure, in particular at pressures between 1 and 100 mbar.

The novel process enables to carry out the production of chloro-benzoyl chlorides in technical scale and high yields using cheap, ready-available educts.

In order to facilitate a further understanding of the invention, the following illustrative examples are presented. The invention is not limited to the specific embodiments described or illustrated, but encompasses the full scope of the appended claims.

EXAMPLE 1

Preparation of 4-chlorobenzoylchloride (PCBO)

A mixture of 115 g 4-chlorobenzotrichloride (CBTC, 0.5 mol) and 1,6 g $FeCl_3$ (10 mmol) is heated to 60° C. 9 g water (0.5 mol) are dosed into the mixture within 1 hours at ambient pressure. After 30 minutes the reaction was complete; the GC analysis showed that the conversion was complete (98 area-% PCBO). In order to determine the yield, the corresponding methyl-ester has been made by adding 1,5 equivalent methanol to the obtained product. The resulting mixture was solved in toluene and washed with 5% aquaous HCl and water. After removing the solvent and recrystalization 83,3 g p-chloromethylbenzoate (98% purity) was formed. Total yield 93%.

EXAMPLE 2

Preparation of 4-chlorobenzoylchloride (PCBO)

A mixture of 460 g 4-chlorobenzotrichloride (CBTC, 2 mol) and 6.5 g $FeCl_3$ (20 mmol) is heated to 50° C. 36 g water (2 mole) are dosed into the mixture within 2 hours at ambient pressure. After 30 minutes the reaction was complete; the GC analysis showed that the conversion was complete (>95 area-% PCBO).

The results of further experiments are given in the following table, in which the conversions have been determined by GC analysis:

TABLE 1

| GC-area % PCBO of mixture | | | |
|---|---|---|---|
| CBTC (mol) | $FeCl_3$ (mol %) | T (° C.) | GC-area % PCBO |
| 1,5 | 2 | 53 | 97 |
| 2 | 2 | 51 | 97 |
| 2 | 2 | 60 | 98 |

In the following eperiments the yield of PCBO has been determined as the actual content of the product given in weight % as shown in Table 2:

TABLE 2

| Weight % PCBO of mixture | | | |
|---|---|---|---|
| CBTC (mol) | $FeCl_3$ (mol %) | T (° C.) | weight % PCBO |
| 2 | 0.5 | 50 | 94.2 |
| 2 | 0.25 | 50 | 95.3 |

Comparison Example

Preparation of 4-chloro-benzoylchloride

A mixture of 460 g 4-chlorobenzotrichloride (CBTC, 2 mol) and 1.0 g $FeCl_3$ (3,08 mmol) is heated to 100° C. 36 g water (2 mol) are dosed into the mixture within 2 hours at ambient pressure. After 30 minutes the analysis showed that the conversion was incomplete (85 weight % PCBO).

What we claim is:

1. A process for the preparation of a chloro-benzoylchloride of formula I

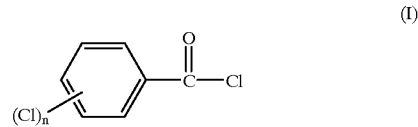

(I)

wherein
n represents an integer of 1, 2 or 3, which process comprises reacting a chloro-trichloromethylbenzene of formula II

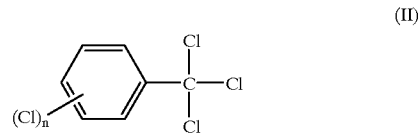

(II)

wherein n has the meaning given above, with about 0.9 to 1.1 molar equivalents of water in the presence of $FeCl_3$ at a temperature from about 45° C. to 65° C.

2. The process according to claim 1, wherein about 1 molar equivalent of water is slowly dosed into a mixture essentially consisting of 1 molar equivalent of the chloro-trichloromethylbenzene of formula II and 0.01 to 3 mol-% of $FeCl_3$ at 45° C. to 65° C.

3. The process according to claim 1, wherein the chloro-trichloromethylbenzene of formula II is reacted with 1 molar equivalent of water.

4. The process according to claim 1, wherein about 0.05 to 5 mol-% of $FeCl_3$ is present.

5. The process according to claim 1, wherein about 0.1 to 3 mol-% of $FeCl_3$ is present.

* * * * *